US011517857B2

(12) United States Patent
Xu et al.

(10) Patent No.: US 11,517,857 B2
(45) Date of Patent: Dec. 6, 2022

(54) METHOD TO MAKE CARBON MOLECULAR SIEVE HOLLOW FIBER MEMBRANES

(71) Applicant: Dow Global Technologies LLC, Midland, MI (US)

(72) Inventors: Liren Xu, Spring, TX (US); Rahul Sharma, Lake Jackson, TX (US); Thomas Fitzgibbons, Lake Jackon, TX (US); Mark K. Brayden, Baton Rouge, LA (US); Marcos V. Martinez, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 4 days.

(21) Appl. No.: 16/634,401

(22) PCT Filed: Mar. 20, 2018

(86) PCT No.: PCT/US2018/023228
§ 371 (c)(1),
(2) Date: Jan. 27, 2020

(87) PCT Pub. No.: WO2019/036064
PCT Pub. Date: Feb. 21, 2019

(65) Prior Publication Data
US 2020/0254393 A1 Aug. 13, 2020

Related U.S. Application Data

(60) Provisional application No. 62/544,993, filed on Aug. 14, 2017.

(51) Int. Cl.
*B01D 67/00* (2006.01)
*B01D 53/22* (2006.01)
*B01D 69/08* (2006.01)
*B01D 71/02* (2006.01)
*C07C 7/144* (2006.01)

(52) U.S. Cl.
CPC ....... *B01D 67/0067* (2013.01); *B01D 53/228* (2013.01); *B01D 67/0055* (2013.01); *B01D 69/08* (2013.01); *B01D 71/021* (2013.01); *C07C 7/144* (2013.01); *B01D 2323/08* (2013.01)

(58) Field of Classification Search
None
See application file for complete search history.

(56) References Cited

U.S. PATENT DOCUMENTS

| 4,113,628 A | 9/1978 | Alegranti |
| 4,127,625 A | 11/1978 | Arisaka et al. |
| RE30,351 E | 7/1980 | Hoehn et al. |
| 4,378,324 A | 3/1983 | Makino et al. |
| 4,460,526 A | 7/1984 | Makino et al. |
| 4,474,662 A | 10/1984 | Makino et al. |
| 4,485,056 A | 11/1984 | Makino et al. |
| 4,512,893 A | 4/1985 | Makino et al. |
| 4,526,770 A | 7/1985 | Pepper et al. |
| 4,671,950 A | 6/1987 | Ogawa et al. |
| 4,705,540 A | 11/1987 | Hayes |
| 4,717,394 A | 1/1988 | Hayes |
| 4,814,129 A | 3/1989 | Imai et al. |
| 4,867,934 A | 9/1989 | Repetti et al. |
| 4,919,860 A * | 4/1990 | Schindler ............. B01D 71/021 210/500.21 |
| 5,085,774 A | 2/1992 | Ekiner et al. |
| 5,089,135 A * | 2/1992 | Yoneyama ......... B01D 67/0067 210/500.23 |
| 5,268,158 A | 12/1993 | Paul, Jr. et al. |
| 5,288,304 A | 2/1994 | Koros et al. |
| 5,820,659 A | 10/1998 | Ekiner et al. |
| 6,565,631 B2 | 5/2003 | Koros et al. |
| 8,591,859 B2 | 11/2013 | León y León |
| 10,150,085 B2 | 12/2018 | Kondo et al. |
| 2001/0035374 A1 | 11/2001 | Yamamoto et al. |
| 2009/0286078 A1* | 11/2009 | Lee ...................... B01D 53/228 428/364 |
| 2013/0152793 A1 | 6/2013 | Bhuwania et al. |
| 2015/0290596 A1* | 10/2015 | Koros ................... B01D 71/64 95/45 |
| 2016/0333502 A1 | 11/2016 | Matsuda et al. |
| 2017/0067186 A1 | 3/2017 | Kia |
| 2017/0203276 A1* | 7/2017 | Liu .................... B01D 67/0067 |

FOREIGN PATENT DOCUMENTS

| DE | 102008038475 A1 | 2/2010 |
| EP | 394449 A1 | 10/1990 |
| EP | 459623 A1 | 12/1991 |

(Continued)

OTHER PUBLICATIONS

International Search Report and Written Opinion pertaining to PCT/US2018/023228, dated Jun. 18, 2018.
Geiszler et al., "Effects of Polyimide Pyrolysis Atmosphere on Separation Performance of Carbon Molecular Sieve Membranes", Ind. Eng. Chem. Res., 1996, 35, 2999.
Steel et al., "Investigation of Porosity of Carbon Materials and Related Effects on Gas Separation Properties", Carbon, 2003, 41, 253.
Steel et al., "An Investigation of the Effects of Pyrolysis Parameters on Gas Separation Properties of Carbon Materials", Carbon, 2005, 43, 1843.

(Continued)

*Primary Examiner* — Jason M Greene
(74) *Attorney, Agent, or Firm* — Dinsmore & Shohl LLP

(57) ABSTRACT

A method of making a hollow fiber carbon molecular sieve is comprised of heating a hollow polymer fiber to a carbonization temperature in an atmosphere that is non-oxidizing to form a hollow fiber carbon molecular sieve, wherein during at least a portion of the heating a tensile force is applied to the hollow polymer fiber. The method may improve the separation of gases similar in size such a propylene from propane.

16 Claims, No Drawings

(56) References Cited

FOREIGN PATENT DOCUMENTS

| | | |
|---|---|---|
| JP | 02074615 A | 3/1990 |
| JP | 2002219344 A | 8/2002 |
| JP | 2003286018 A | 4/2009 |
| KR | 10-2016-0070087 A | 6/2016 |
| WO | 2015100161 A | 7/2015 |
| WO | 2016003680 A1 | 1/2016 |
| WO | WO 2016003680 A1 * 1/2016 ............. B01D 53/02 |
| WO | 2017105836 A1 | 6/2017 |
| WO | 2017165098 A1 | 9/2017 |
| WO | 2018089114 A1 | 5/2018 |

OTHER PUBLICATIONS

Suda et al., "Gas Permeation Through Micropores of Carbon Molecular Sieve Membranes Derived From Kapton Polyimide," J. Phys. Chem. B, 1997, 101, 3988.

Examination Report pertaining to corresponding G.C.C. Patent Application No. 2018-35812, dated Jan. 15, 2020.
English Translation of Chinese Office Action dated Sep. 27, 2021, pertaining to Chinese Patent Application No. 201880059885.9 (9 pgs).
English Translation of Japanese Office Action dated Jan. 18, 2022, pertaining to JP Patent Application No. 2020-505895, 6 pgs.
English Translation of Chinese Office Action dated Feb. 22, 2022, pertaining to CN Patent Application No. 201880059885.9, 12 pgs.
Chinese Office Action dated Jun. 20, 2022 for Chinese Patent Application No. 201880059885.9 (English translation of Final Rejection—12 total pages).
Brazil Office Action dated May 31, 2022 for Brazilian Patent Application No. BR112020002664-6 4 total pages.
Japanese Office Action dated Jun. 14, 2022 for Japanese Patent Application No. 2020-505895 (English translation 3 total pages).
Korean Office Action dated Sep. 19, 2022 for Korean Patent Application No. 10-2020-7006294 (English summary—6 total pages).

* cited by examiner

METHOD TO MAKE CARBON MOLECULAR SIEVE HOLLOW FIBER MEMBRANES

FIELD OF THE INVENTION

The invention relates to carbon molecular sieve (CMS) membranes for use in gas separation. In particular the invention relates to a method for producing CMS membranes from polyimides.

BACKGROUND OF THE INVENTION

Membranes are widely used for the separation of gases and liquids, including for example, separating acid gases, such as $CO_2$ and $H_2S$ from natural gas, and the removal of $O_2$ from air. Gas transport through such membranes is commonly modeled by the sorption-diffusion mechanism. Currently, polymeric membranes are well studied and widely available for gaseous separations due to easy process-ability and low cost. CMS membranes, however, have been shown to have attractive separation performance properties exceeding that of polymeric membranes.

Polyimides have been pyrolyzed to form CMS membranes under many differing conditions. U.S. Pat. No. 6,565,631 discloses pyrolyzing under vacuum and inert gases with trace amounts of oxygen. Other patents describe processes for producing carbon membranes (both asymmetric hollow "filamentary" and flat sheets), and applications for gas separation, include, for example, U.S. Pat. No. 5,288,304, and EP Patent No. 0459623. Steel and Koros performed a detailed investigation of the impact of pyrolysis temperature, thermal soak time, and polymer composition on the performance of carbon membranes. (K. M. Steel and W. J. Koros, *Investigation of Porosity of Carbon Materials and Related Effects on Gas Separation Properties, Carbon*, 41, 253 (2003); K. M. Steel and W. J. Koros, *An Investigation of the Effects of Pyrolysis Parameters on Gas Separation Properties of Carbon Materials, Carbon*, 43, 1843 (2005)). In these works membranes were produced in an air atmosphere at 0.03 mm Hg pressure.

The impact of pyrolysis atmosphere has been researched. Suda and Haraya disclosed the formation of CMS membranes under different environments. (H. Suda and K. Haraya, *Gas Permeation Through Micropores of Carbon Molecular Sieve Membranes Derived From Kapton Polyimide, J. Phys. Chem. B*, 101, 3988 (1997).) Similarly, Geiszler and Koros disclosed the results of CMS fibers produced from pyrolysis of fluorinated polyimide in helium and argon for both $O_2/N_2$ and $H_2/N_2$ separations. (V. C. Geiszler and W. J. Koros, *Effects of Polyimide Pyrolysis Atmosphere on Separation Performance of Carbon Molecular Sieve Membranes, Ind. Eng. Chem. Res.*, 35, 2999 (1996)). Recently, the effect of heating and cooling rate have been described on the pyrolysis of polyimides in copending WO PCT/US17/020432 application.

SUMMARY OF THE INVENTION

Applicants have surprisingly discovered that the application of a tensile force along the length during pyrolysis of a hollow polymer fiber to form a hollow fiber CMS membrane leads to improved separation performance for commercially valuable difficult to separate gas molecules such as propylene from propane.

A method of making a hollow fiber carbon molecular sieve comprising,
(i) providing a hollow polymer fiber,
(ii) heating the hollow polymer fiber to a carbonization temperature in an atmosphere that is non-oxidizing to form a hollow fiber carbon molecular sieve, wherein during at least a portion of the heating a tensile force is applied to the hollow polymer fiber.

Surprisingly, the method of the invention may improve the ability of the hollow fiber CMS membrane to separate gas molecules that are difficult to separate due to their close size (e.g., propylene from propane). That is, the selectivity/permeance characteristics (productivity) may be improved relative to hollow fiber membranes carbonized in the absence of an applied tensile force along the length of the fiber.

A second aspect of this invention is a process for separating a gas molecule from a gas feed comprised of the gas molecule and at least one other gas molecule comprising
(i) providing the hollow fiber carbon molecular sieve produced by the method of the first aspect; and
(ii) flowing the gas feed through said hollow fiber carbon molecular sieve to produce a first stream having an increased concentration of the gas molecule and a second stream having an increased concentration of the other gas molecule.

A third aspect is a gas separating module comprising a sealable enclosure comprised of: a plurality of hollow fiber carbon molecular sieves, comprising at least one hollow fiber carbon molecular sieve of the first aspect, contained within the sealable enclosure; an inlet for introducing a gas feed comprised of at least two differing gas molecules; a first outlet for permitting egress of a permeate gas stream; and a second outlet for egress of a retentate gas stream.

The gas separation method is particularly useful for separating gas molecules in gas feeds that have very similar molecular sizes such as ethane/ethylene and propane/propylene. It may also be used to separate gases from atmospheric air such as oxygen, nitrogen, or carbon dioxide or separating gases (e.g., methane) in natural gas feeds.

DETAILED DESCRIPTION OF THE INVENTION

The method entails providing a hollow polymer fiber to be carbonized to form the hollow fiber carbon molecular sieve (CMS) membrane. The polymer may be any polymer suitable in forming a hollow fiber and that may be carbonized to make the hollow fiber CMS membrane. Exemplary polymers include cellulosic polymers, polyvinylidene chloride polymers and copolymers such as described by WO/2016/003680 and polyimides. In an embodiment, the hollow polymer fiber is a hollow fiber having a thin dense layer on the outer surface of the fiber and a thicker porous support layer on the inner surface of the fiber, which is typically referred to as an asymmetric hollow fiber. Desirably, the hollow fibers are substantially defect-free. "Defect-free" is determined to be when the selectivity of a gas pair, typically oxygen ($O_2$) and nitrogen ($N_2$), through a hollow fiber membrane is at least 90 percent of the selectivity for the same gas pair through a dense film prepared from the same composition as that used to make the polymeric precursor hollow fiber membrane.

When making the polymer hollow fiber and in particular a polyimide hollow fiber, conventional procedures known in the art may be used (see, for example U.S. Pat. Nos. 5,820,659; 5,085,774; 4,127,625; 4,867,934; 4,113,628;

4,378,324; 4,460,526; 4,474,662; 4,485,056; 4,512,893 and 4,717,394). Exemplary methods include coextrusion procedures such as a dry-jet/wet-quench spinning process (in which an air gap exists between the tip of the spinneret and the coagulation or quench bath) or a wet spinning process (with zero air-gap distance) may be used to make the hollow fibers.

Illustratively to make the polymer hollow fiber, a dope solution is prepared for the spinning process where the dope solution is comprised of the polymer and solvents. When making a hollow fiber, typically the dope solution is a mixture of solvents that solubilize the polymer and illustratively polyimide and a second solvent that does not solubilize (or solubilizes to a limited extent) the polyimide, but is soluble with the solvent that solubilizes the polyimide are used. Exemplary solvents that are useful to solubilize the polyimide include polar aprotic solvents such as N-Methyl-2-pyrrolidone (NMP), tetrahydrofuran (THF), dimethylacetamide (DMAc) and dimethylformamide (DMF). Exemplary solvents that do not solubilize the polyimide, but are soluble with the solvents that do solubilize the polyimide include methanol, ethanol, water, 1-propanol. To facilitate the practical formation of the hollow fiber, generally, the polyimide needs to be dissolved in an amount of at least about 10% to 40% by weight of the dope solution. Desirably the amount of polyimide solubilized is at least 12%, 15%, 18% or 20%. Such dope solutions typically consist of both non-volatile solvents and volatile solvents. The evaporation of the volatile solvents (boiling point <100° C.) in the air gap promotes the formation of a dense skin layer on the outer surface of the fiber and thus creates the asymmetric fiber structure.

The polyimide, when used, may be any polyimide. In a particular embodiment the polyimide has a storage modulus minimum at a temperature greater than 250° C. that is less than the storage modulus at a temperature of 250° C., but no more than 500 times less measured using dynamic mechanical thermal analysis from 250° C. to a temperature where the polyimide carbonizes. Preferably, the storage is no more than 100, 50, 20, 10, 7.5 or even 5 times less. It has been discovered that the smaller minimum allows for the carbonization under tension to be more controlled due to a more manageable strain associated with larger moduli minimums. Without being bound in any way, the storage modulus minimum above 250° C. may be or could be correlated or attributed with the polyimide undergoing glass transition or the like prior to carbonizing. The temperature where the polyimide carbonizes (temperature where the polyimide starts to decompose and form carbon in a non-oxidizing atmosphere) may vary, but in general the temperature is above 400° C. and inevitably will carbonize at a temperature at or above 500° C. or 550° C. The polyimide preferably is a thermoplastic.

The dynamic mechanical thermal analysis is performed using a thin film sample of the polyimide having general dimensions that are 15 mm long, 5 mm wide, and 0.022 mm thick. The samples are kept under $N_2$ purge during the measurements. The films are first heated to 250° C. and equilibrated at this temperature for 15 minutes. Thereafter temperature is ramped to 535° C. at the rate of 4° C./minute, and finally to 550° C. at the rate of 0.25° C./minute. The oscillation frequency is set at 6.28 rad/s and the strain amplitude is set at 0.1%. An exemplary dynamic mechanical thermal analyzer that may be used is RSA III rheometer from TA Instruments, New Castle, Del.

Generally, polyimides having the storage modulus characteristic described above are aromatic polyimides. Aromatic polyimides that may be useful are described by U.S. Pat. No. 4,983,191 from col. 2, line 65 to col. 5, line 28. Other aromatic polyimides that may be useful are described by U.S. Pat. Nos. 4,717,394; 4,705,540; and re30351. Desirable aromatic polyimides typically are a reaction product of a dianhydride and a diamine, which is understood to proceed by forming a polyamic acid intermediate that is subsequently ring-closed to form the polyimide by chemical and/or thermal dehydration. Preferably, the dianhydride is comprised of a dianhydride having no rotational freedom within the dianhydride, which means that there are no single bonds between aromatic moieties, which would allow the aromatic rings to rotate in relation to each other. In another embodiment, each of the dianhydrides used to make the polyimide has no rotational freedom. In another embodiment, the dianhydride is a combination of dianhydrides that have and do not have rotational freedom. Examples of dianhydrides having no rotational freedom include pyromellitic dianhydride (PMDA) and 1,4,5,8-naphthalene tetracarboxylic dianhydride (NTDA). Examples of a dianhydride having rotational freedom include benzophenone-3,3',4,4'-tetracarboxylic dianhydride (BTDA), 5,5'-[2,2,2-trifluoro-1-(trifluoromethyl)ethylidene]-1,3-isobenzofurandione (6FDA) and 3,3',4,4'-biphenyl tetracarboxylic dianhydride (BPDA). Combinations of aromatic dianhydrides are contemplated.

The diamine used to make the polyimide may have rotational freedom or not. In a particular embodiment, the diamine is comprised of diamines having rotational freedom and diamines not having rotational freedom (diamines having a single aromatic ring are included in those diamines that have no rotational freedom in the same manner as described for the dianhydrides above). It is desirable for the diamine to have no rotational freedom and, in particular, of an aromatic diamine having only one aromatic ring. Examples of diamines having no rotational freedom include 2,4,6-trimethyl-1,3-phenylenediamine (DAM), 3,5-diaminobenzoic acid (DABA), 2,3,5,6-tetramethyl-1,4-phenylenediamine (durene), dimethyl-3,7-diaminodiphenyl-thiophene-5,5'-dioxide (DDBT), meta-phenylenediamine (m-PDA), para-phenylenediamine, and 2,4-diaminotoluene (2,4-DAT). Examples of diamines having rotational freedom include 4,4'-oxydianiline (ODA), tetramethylmethylenedianiline (TMMDA), and 4,4'-diamino 2,2'-biphenyl disulfonic acid (BDSA).

In a particular embodiment, the polyimide is the reaction product of a combination of dianhydrides with some having rotational freedom and some not having rotational freedom and a diamine having no rotational freedom and in particular an aromatic diamine that has only one aromatic ring. A particular embodiment of such a polyimide is exemplified by the polyimide 6FDA/PMDA-DAM as represented in below Formula 1:

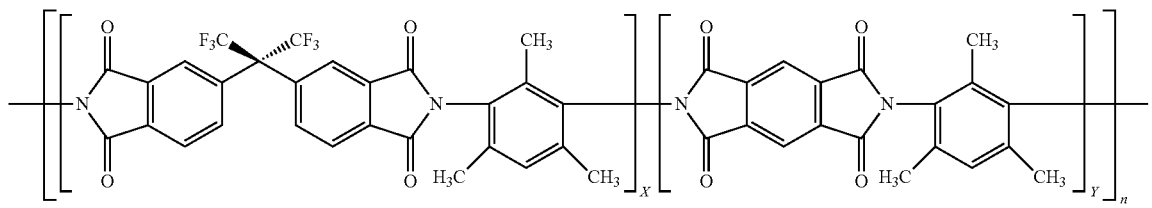

where X and Y represent the mole fraction of each dianhydride used to make the polyimide with X and Y adding up to 1 and n represents an integer representing the number of repeat units and n may be any value to realize the weight average molecular weight described herein. Desirably, Y is from 0.25, 0.3 or 0.4 to 0.9, 0.8 or 0.75. Each of the monomers used to make 6FDA/PMDA-DAM is commercially available for example from Sigma-Aldrich Co. LLC, St. Louis, Mo. or TCI America, Portland, Oreg. The formation of such polyimides is further described in copending U.S. Provisional Appl. No. 62/420,285 filed Nov. 10, 2016.

Generally, the polyimide has a molecular weight sufficient to form a polyimide fiber having the requisite strength to be handled and subsequently pyrolyzed, but not so high that it becomes impractical to dissolve to make a dope solution able to form the hollow fiber. Typically, the weight average ($M_w$) molecular weight of the polyimide is 30 to 200 kDa, but desirably the molecular weight of 40 to 70 kDa. Polymer molecular weight may be controlled by stoichiometry of dianhydride to diamine monomers, monomer purity, as well as use of monofunctional endcapping agents such as monoamines (i.e., aniline, 3-ethynylaniline) and monoanhydrides (i.e., phthalic anhydride, succinic anhydride, maleic anhydride).

After the dope solution is formed, the solution is shaped into a hollow fiber as described above. After shaping, the solvents may be exchanged with other solvents (such as methanol and hexane) to prevent, for example, pore collapse, and the solvents are further removed by any convenient method such as application of heat at temperatures below where the polymer decomposes, oxidizes or carburizes, vacuum, flowing gases or combination thereof and include those known in the art.

The hollow polymer fiber such as described above is pyrolyzed by heating to a carbonization temperature to form the hollow fiber carbon molecular sieve. It is understood that at the carbonization temperature, the hollow fiber carbon molecular sieve may still have a small amount of other atoms present in the polymer such as nitrogen. During pyrolysis to the carbonization temperature, a tensile force is applied along the length of the hollow fiber. The pyrolysis may be performed in a batch or continuous mode. In a batch mode, the tensile force may be applied by any suitable method such as hanging a weight or employing a screw mechanism attached to a pressure transducer or attached to a rotatable spool, which may be controlled by known commercially available process control. Alternatively, the force may arise from constraining the fiber in the length direction and due to shrinkage that may occur during the heating a tensile force is realized. Likewise the pyrolysis may be performed in a continuous mode by known methods such as employing independently driven feed and take up rolls or spools with the rotational speed of each being variable along with use of torque transducers or known tensioning roll devices to control the tensile force being applied. Exemplary continuous methods and apparatus for applying tension to structural solid fibers may be used such as those described by U.S. Pat. Nos. 4,526,770; 4,671,950; 4,814,129; 5,268,158; 8,591,859 and U.S. Pat. Appl. No. 2016/0333502.

In an embodiment, a tensile force is applied for the duration of the heating from room temperature to the carbonization temperature. The tensile force may be varied during different temperature regimes during the heating. In another embodiment the tensile force is applied until a set elongation is achieved during the heating of the polymer hollow fiber and no or tensile force is maintained to maintain that elongation until the formed hollow fiber CMS membrane is cooled. Illustratively, there may be no tensile force applied or a different tensile force applied up to the point where the hollow fiber polymer begins to decompose and carbonize. This onset carbonization temperature is dependent on the particular polymer used and other factors such as heating rate and is readily determinable by one of ordinary skill in the art. At a temperature below the onset carbonization temperature, the polymer may undergo cross-linking to make the polymer a thermoset and to yield a higher percentage of carbon at the carbonization temperature. This heating to below the carbonization onset temperature is referred to as pretreatment heating to a pretreatment temperature herein (typically below about 400° C. or 300° C.). In an embodiment, the polymer is a PVDC copolymer that is heated to a pretreatment temperature where the PVDC copolyomer dehydrochlorinates as described in WO/2016/003680 page 6, line 30 to page 7, line 22 incorporated herein by reference. During heating to such pretreatment temperatures (i.e., temperature below where the polymer begins to carbonize) atmospheres comprised of oxygen including air (wet or dry) may be desirable or the atmosphere may be one of those described below when heating to the carbonization temperature. A tensile force may be applied during the entire heating to the pretreatment temperature or only for a portion and the force may varied depending the temperature. Likewise, during the heating to the carbonization temperature the tensile force may be applied for the entire duration of the heating including cooling or only a portion with it being contemplated that the force may be varied depending on the temperature.

The amount of tension applied is dependent on several factors such as the temperature regime of the heating cycle and the mechanical properties of the fiber as the fiber carbonizes. Nevertheless, the tension applied should not be so great as to rupture the hollow fiber or stretch is so far that it ceases to be a hollow fiber. In a preferred embodiment, the polymer as detailed above has a storage modulus minimum at a temperature greater than 250° C. that is less than the storage modulus at a temperature of 250° C., but no more than 10 or even 5 times less measured using dynamic mechanical thermal analysis from 250° C. to a temperature where the polyimide carbonizes. This mechanical behavior allows for the tension applied to be consistent throughout the duration of the heating without having concern for over-stretching the hollow fiber or rupturing it. Typically, without being limiting, the amount of tension may range from just above 0 to $25 \times 10^6$ N/m², but to reiterate is dependent on the mechanical behavior of the polymer of the hollow fiber as it is heated. That is the upper range of applied tension may be applied when the polymer has significantly carbonized with the elastic modulus substantially increasing compared to the polymer hollow fiber prior to it carbonizing or during the carbonization.

It has been surprisingly discovered that the application of tension may improve the separation performance of the hollow fiber CMS membrane for difficult to separate commercially valuable gas molecules such as olefins from their paraffin analogs and in particular the smaller olefins (e.g., ethylene and propylene) from ethane and propane respectively.

The hollow polymer fibers may be pyrolyzed under various inert or vacuum conditions, preferably under inert gas purge conditions, for the vacuum pyrolysis, preferably at low pressures (e.g., less than 0.1 millibar). U.S. Pat. No. 6,565,631 and co-pending U.S. provisional application 62/310,836, illustratively, describe a suitable heating method for pyrolysis of the polyimide fibers to form the CMS hollow fibers, and each is incorporated herein by reference. A carbonization temperature of between about 450° C. to about 800° C. may advantageously be used. The carbonization temperature may be adjusted in combination with the pyrolysis atmosphere to tune the performance properties of the resulting CMS hollow fiber membrane. For example, the carbonization temperature may be 1000° C. or more. Optionally, the pyrolysis temperature is maintained between about 500° C. and about 550° C. or 650° C. The pyrolysis soak time (i.e., the duration of time at the pyrolysis temperature) may vary (and may include no soak time) but advantageously is between about 1 hour to about 10 hours, alternatively from about 2 hours to about 8 hours, alternatively from about 4 hours to about 6 hours. An exemplary heating protocol may include starting at a first set point of about 70° C., then heating to a second set point of about 250° C. at a rate of about 13.3° C. per minute, then heating to a third set point of about 535° C. at a rate of about 3.85° C. per minute, and then a fourth set point of about 550° C. at a rate of about 0.25° C. per minute. The fourth set point is then optionally maintained for the determined soak time. After the heating cycle is complete, the system is typically allowed to cool while still under vacuum or in a controlled atmosphere.

In one embodiment the pyrolysis utilizes a controlled purge gas atmosphere during pyrolysis in which low levels of oxygen are present in an inert gas. By way of example, an inert gas such as argon is used as the purge gas atmosphere. Other suitable inert gases include, but are not limited to, nitrogen, helium, or any combinations thereof. By using any suitable method such as a valve, the inert gas containing a specific concentration of oxygen may be introduced into the pyrolysis atmosphere. For example, the amount of oxygen in the purge atmosphere may be less than about 50 ppm (parts per million) $O_2$/Ar. Alternatively, the amount of oxygen in the purge atmosphere may be less than 40 ppm $O_2$/Ar. Embodiments include pyrolysis atmospheres with about 8 ppm, 7 ppm, or 4 ppm $O_2$/Ar.

After pyrolyzing, the hollow fiber CMS membrane that has formed is cooled to a temperature where no further pyrolysis occurs. Generally, this is a temperature where no decomposition products would be evolved from the precursor polymer and may vary from polymer to polymer. Generally, the temperature is 200° C. or less and typically the temperature is taken as 100° C., 50° C. or essentially typical ambient temperatures (20 to 40° C.). The cooling may be at any useful rate, such as passively cooling (e.g., turning off the power to furnace and allowing to cool naturally). Alternatively, it may be desirable to more rapidly cool such as using known techniques to realize faster cooling such as removing insulation, or using cooling fans or employment of water cooled jackets.

After cooling, the CMS hollow fiber membrane may be subjected to a further treatment, for example, to make the fiber more stable or improve particular permeance/selectivity for particular gases. Such further treatments are described in pending provisional U.S. application 62/268,556, incorporated herein by reference.

The gas permeation properties of a membrane can be determined by gas permeation experiments. Two intrinsic properties have utility in evaluating the separation performance of a membrane material: its "permeability," a measure of the membrane's intrinsic productivity; and its "selectivity," a measure of the membrane's separation efficiency. One typically determines "permeability" in Barrer (1Barrer=$10^{-10}$[cm³(STP)cm]/[cm²s cmHg], calculated as the flux ($n_i$) divided by the partial pressure difference between the membrane upstream and downstream ($\Delta p_i$), and multiplied by the thickness of the membrane (l).

$$P_i = \frac{n_i l}{\Delta p_i}$$

Another term, "permeance", is defined herein as productivity of asymmetric hollow fiber membranes and is typically measured in Gas Permeation Units (GPU) (1GPU= $10^{-6}$[cm³(STP)]/[cm²s cmHG]), determined by dividing permeability by effective membrane separation layer thickness.

$$\left(\frac{P_i}{l}\right) = \frac{n_i}{\Delta p_i}$$

Finally, "selectivity" is defined herein as the ability of one gas's permeability through the membrane or permeance relative to the same property of another gas. It is measured as a unitless ratio.

$$\alpha_{i/j} = \frac{P_i}{P_j} = \frac{(P_i/l)}{(P_j/l)}$$

The CMS membranes are particularly suitable for separating gases that are similar in size such as described above and involve flowing a gas feed containing a desired gas molecule and at least one other gas molecule through the CMS membrane. The flowing of the gas results in a first stream having an increased concentration of the desired gas molecule and, a second stream having an increased concentration of the other gas molecule. The process may be utilized to separate any of the aforementioned gas pairs and in particular is suitable for separating ethylene and ethane or propylene and propylene. When practicing the process, the CMS membrane is desirably fabricated into a module comprising a sealable enclosure comprised of a plurality of carbon molecular sieve membranes that is comprised of at least one carbon molecular sieve membrane produced by the method of the invention that are contained within the sealable enclosure. The sealable enclosure has an inlet for introducing a gas feed comprised of at least two differing gas molecules; a first outlet for permitting egress of a permeate gas stream; and a second outlet for egress of a retentate gas stream.

EXAMPLES

Polymer Hollow Fiber Formation 1 (PHF 1)

A polymer hollow fiber 1 was made using a 6FDA:BPDA-DAM (1:1) polymer. The 6FDA:BPDA-DAM was acquired from Akron Polymer Systems, Akron, Ohio. Gel permeation chromatography was performed to evaluate the molecular weight. Tosoh TSKgel Alpha-M columns were used with 0.5 mL/min eluent of dimethylformamide (DMF) with 4 g/L lithium nitrate. Waters 2695 separation module/Viscotek TDA 302 interface/Waters 2414 RI detector was used as the detector and was at 40° C. The polymer was dissolved in DMF at 0.25 wt %, and the sample injection volume was 100 µL. Agilent PEO/PEG EasiCal standards were used for calibration. The polymer had a weight average molecular weight ($M_w$) of 83 kDa and polydispersity index (PDI) of 5.2. The polymer was dried under vacuum at 110° C. for 24 hours and then a dope was formed. The dope was made by mixing the 6FDA:BPDA-DAM polymer with solvents and compounds in Table 1 and roll mixed in a Qorpak™ glass bottle sealed with a polytetrafluoroethylene (TEFLON™) cap and a rolling speed of 5 revolutions per minute (rpm) for a period of about 3 weeks to form a homogeneous dope.

TABLE 1

PHF 1 Dope formulation

| Dope Component | weight % | mass (g) |
| --- | --- | --- |
| Comp. Ex. 1 Polyimide | 25 | 50 |
| NMP | 43 | 86 |
| THF | 10 | 20 |
| EtOH | 22 | 44 |

NMP = N-Methyl-2-pyrrolidone;
THF = Tetrahydrofuran;
EtOH = Ethanol

The homogeneous dope was loaded into a 500 milliliter (mL) syringe pump and allowed to degas overnight by heating the pump to a set point temperature of 50° C. using a heating tape.

Bore fluid (80 wt % NMP and 20 wt % water, based on total bore fluid weight) was loaded into a separate 100 mL syringe pump and then the dope and bore fluid were co-extruded through a spinneret operating at a flow rate of 100 milliliters per hour (mL/hr) for the dope, and 100 mL/hr for the bore fluid, filtering both the bore fluid and the dope in line between delivery pumps and the spinneret using 40 µm and 2 µm metal filters. The temperature was controlled using thermocouples and heating tape placed on the spinneret, dope filters and dope pump at a set point temperature of 70° C.

After passing through a two centimeter (cm) air gap, the nascent fibers that were formed by the spinneret were quenched in a water bath (50° C.) and the fibers were allowed to phase separate. The fibers were collected using a 0.32 meter (m) diameter polyethylene drum passing over TEFLON guides and operating at a take-up rate of 5 meters per minute (m/min).

The fibers were cut from the drum and rinsed at least four times in separate water baths over a span of 48 hours. The rinsed fibers in containers and effect solvent exchange three times with methanol for 20 minutes and then hexane for 20 minutes before recovering the fibers and drying them under argon purge at a set point temperature of 100° C. for two hours.

Prior to pyrolyzing the fibers, a sample quantity of the above fibers (also known as "precursor fibers") were tested for skin integrity. One or more hollow precursor fibers were potted into ¼ inch (0.64 cm) (outside diameter, OD) stainless steel tubing. Each tubing end was connected to a ¼ inch (0.64 cm) stainless steel tee; and each tee was connected to ¼ inch (0.64 cm) female and male NPT tube adapters, which were sealed to NPT connections with epoxy. The membrane modules were tested using a constant pressure permeation system. Argon was used as sweep gas in the permeate side. The flow rate of the combined sweep gas and permeate gas was measured by a Bios Drycal flowmeter, while the composition was measured by gas chromatography. The flow rate and composition were then used for calculating gas permeance. The selectivity of each gas pair as a ratio of the individual gas permeance was calculated. The mixed gas feed used for precursor defect-free property examination was 10 mol % $CO_2$/90 mol % $N_2$. The permeation unit was maintained at 35° C., and the feed and permeate/sweep pressures were kept at 52 and 2 psig, respectively.

In addition, the polyimide was cast into a film and cut into pieces of having dimensions that are 15 mm long, 5 mm wide, and 0.022 mm thick and dynamic mechanical thermal analysis was performed on the film as follows. Dynamic Mechanical Thermal Analysis (DMTA) was carried out on the polyimide films in tension mode using a RSA III rheometer from TA Instruments. The films were kept under a $N_2$ purge during the measurements. The films were first heated to 250° C. and equilibrated at this temperature for 15 minutes. Thereafter temperature was ramped to 535° C. at the rate of 4° C./minute, and finally to 550° C. at the rate of 0.25° C./minute. The oscillation frequency was set at 6.28 rad/s and strain amplitude at 0.1%. The results of the DMTA tests are shown in Table 3.

Polymer Hollow Fiber Formation 2 (PHF 2)

A 6FDA/PMDA-DAM polyimide having a mole ratio of 6FDA/PMDA of 1/3 (25%/75%) was made as follows. Into a 3 neck 2 L flask with a slow $N_2$ sweep, 611 grams of 1-methyl-2-pyrrolidinone (611 grams), toluene (50 mL) were loaded and stirred with a magnetic stirring bar. Toluene was distilled from the mixture into a Dean-Stark type trap and drained. The apparatus was cooled to room temperature while stirring. The Dean-Stark type trap was removed and the flask was placed under positive $N_2$. Vacuum sublimed pyromellitic dianhydride (40.887 grams, 0.18745 mol), vacuum sublimed 4,4'-(hexafluoroisopropylidene)diphthalic anhydride (27.751 grams, 62.468 mmol), vacuum sublimed maleic anhydride (0.574 gram, 5.85 mmol), and 2,4,6-trimethyl-m-phenylene diamine (37.976 grams, 0.25280 mol) were added to the flask with 10 mL of dry 1-methyl-2-pyrrolidinone used to rinse down monomers. After ~44 hours reacting under overhead stirring, the inherent viscosity of polyamic acid was 0.73 dL/g (0.1064 g/dL, 30.0° C., 1-methyl-2-pyrrolidinone). To the stirred polyamic acid solution dry 3-picoline (25.8 mL) was injected with a solution of 1-methyl-2-pyrrolidinone (226 mL) and acetic anhydride (226 mL) added dropwise over ~2 hours with stirring continuing overnight. The polyimide product was isolated by precipitation in stirred methanol (~6 L) with polyimide being collected by filtration and subsequently washed four times with fresh methanol. The polyimide product was dried to a constant weight in a ~100° C. vacuum oven with a recovered yield of 94 grams. Inherent viscosity of the polyimide was 0.75 dL/g (0.1044 g/dL, 30.0° C., 1-methyl-2-pyrrolidinone). Using the same GPC conditions, the polymer $M_w$ was found to be 46.7 kDa and PDI was 3.0.

Hollow fibers were formed and the polyimide was tested as described for PHF 1 using the dope composition as shown in Table 2 and following conditions: 180 mL/hr dope flow rate, 60 mL/hr bore fluid flow with a composition of 95 wt % NMP/5 wt % $H_2O$, 70° C. spinneret temperature, 50° C. quench bath temperature, 15 cm air gap, 10 m/min take-up rate.

TABLE 2

| PHF 2 Dope formulation | | |
|---|---|---|
| Dope Component | wt % | mass (g) |
| Comparative Example 2 Polyimide | 25 | 50 |
| NMP | 58 | 116 |
| THF | 10 | 20 |
| EtOH | 7 | 14 |

TABLE 3

|  | PHF 1 | PHF 2 |
|---|---|---|
| Storage modulus at 250° C. (Pa) | $1.83 \times 10^9$ | $1.80 \times 10^9$ |
| Minimum storage modulus (Pa) | $4.79 \times 10^7$ | $9.20 \times 10^8$ |
| Ratio | 38.2 | 2.0 |

EXAMPLES

PHF 1 and 2 were pyrolyzed to form the hollow fiber CMS membranes by placing the PHF 1 and 2 fibers horizontally in a tube furnace that were gripped on each end by a metal gripper. One gripper was anchored on one end of the tube furnace to a flange that was configured to allow the furnace to be purged with ultrahigh purity argon at a flow rate of 500 standard cubic centimeters per minute (sccm). The other gripper was attached to a wire running through a flange at the other end where by the wire was engaged with a pulley such that a weight could be attached to the metal wire to apply a tensile force by gravity to the polymer hollow fibers during heating of the tube furnace. The central heating zone (zone 2) of the tube furnace had a heating schedule shown in Table 4 to carbonize the polymer hollow fibers. End heating zones (zones 1 and 3) are also shown in Table 4 and were used to protect the metal wires and grips used. Prior to pyrolyzing the furnace was purged of oxygen by evacuating and then purging the tube furnace for a minimum of six hours to reduce the oxygen level to less than 5 ppm. After the soak time, the furnace was shut off, cooled under the flowing argon (passively cooled), which typically cooled in about 4 to 6 hours. The tensile force as given by the weight is shown in Tables 5 and 6. Typically, the amount of fibers in each pyrolysis was 4.

TABLE 4

| zone 1 | | | zone 2 | | | zone 3 | | |
|---|---|---|---|---|---|---|---|---|
| start ° C. | end ° C. | ramp rate ° C./min | start ° C. | end ° C. | ramp rate ° C./min | start ° C. | end ° C. | ramp rate ° C./min |
| preheat to 70° C. | | | preheat to 70° C. | | | preheat to 70° C. | | |
| 70 | 250 | 13.3 | 70 | 250 | 13.3 | 70 | 250 | 13.3 |
| 250 | 345 | 3.85 | 250 | 535 | 3.85 | 250 | 340 | 3.85 |
| 345 | 360 | 0.25 | 535 | 550 | 0.25 | 340 | 350 | 0.25 |
| Soak at 360° C. for 2 hours | | | Soak at 550° C. for 2 hours | | | Soak at 360° C. for 2 hours | | |

After cooling the fibers were removed from the furnace and potted into modules as described above. The modules were allowed at least 2 hours to set before being loaded into the permeation testing system for initial tests. All permeation tests were determined using a 50:50 mixture of propylene and propane, or ethylene and ethane, or hydrogen and ethylene in a constant pressure system described above with 52 psig upstream and downstream at 2 psig argon sweep at 35° C. The stage cut was maintained at less than 1%. For each test, the permeation was run multiple hours and most of time more than 20 hours for stable performance. The permeance and selectivity results are shown in Tables 5 and 6.

From these Tables it is readily apparent that the propylene/propane separation is substantially improved for hollow fiber CMS membranes produced under tension (Example 1 compared to Comparative Example 1). Likewise, Example 2, which had substantially more stretching under a tensile force until a set elongation was reached (25%) had substantially improved hydrogen/ethylene selectivity. From this it is apparent that the tensile force and how it is applied will render desirable results for targeted separations. Likewise, when using a differing polyimide PHF 2, similar improvements in particular selectivities are evident (propylene/propane) when applying a tensile force.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims, which even though may not depend directly from each and every other, it is understood that any all combinations are contemplated. Although specific terms are employed herein, they are used in a generic and descriptive sense only and not for purposes of limitation.

TABLE 5

Permeance/Selectivity of Carbonized PHF 1 Membranes

| Example | Tension g/fiber | Length change % | OD change % | $C_2H_4$ (GPU) | $\alpha(C_2H_4/C_2H_6)$ | $H_2$ (GPU) | $\alpha(H_2/C_2H_4)$ | $C_3H_6$ (GPU) | $\alpha(C_3H_6/C_3H_8)$ |
|---|---|---|---|---|---|---|---|---|---|
| Comp. 1 | 0 | −24.8 | −13.5 | 17.2 ± 2.8 | 5.3 ± 0.2 | 330 ± 122 | 22.8 ± 6.6 | 13.3 ± 0.6 | 17.1 ± 0.3 |
| 1 | 5 | <1 | −22.3 | 9.1 ± 0.4 | 5.4 ± 1.3 | 218.0 ± 5.2 | 20.8 ± 2.1 | 5.7 ± 1.8 | 24.3 ± 2.5 |
| 2 | 50 (length control at 25% elongation) | 25.0 | −43.2 | 2.3 ± 0.4 | 5.4 ± 0.4 | 200.7 ± 19.4 | 60.4 ± 2.7 | 1.4 ± 0.2 | 21.1 ± 10.7 |

TABLE 6

Permeance/Selectivity of Carbonized PHF 2 Membranes

| Example | Tension g/fiber | Length change % | OD change % | $C_2H_4$ (GPU) | $\alpha(C_2H_4/C_2H_6)$ | $H_2$ (GPU) | $\alpha(H_2/C_2H_4)$ | $C_3H_6$ (GPU) | $\alpha(C_3H_6/C_3H_8)$ |
|---|---|---|---|---|---|---|---|---|---|
| Comparative 2 | 0 | −20.8 | −17.2 | 13.2 ± 6.4 | 5.7 ± 0.5 | 406.3 ± 31.5 | 39.1 ± 22.7 | 11.2 ± 4.0 | 22.2 ± 3.0 |
| 3 | 50 | <1 | −13.9 | 10.6 ± 1.3 | 5.5 ± 0.1 | 407.5 ± 9.2 | 37.9 ± 3.0 | 5.3 ± 0.6 | 31.1 ± 4.8 |

What is claimed is:

1. A method of making a hollow fiber carbon molecular sieve membrane comprising,
    (i) providing a hollow polymer fiber comprised of a polyimide, wherein the polyimide is the reaction product of a dianhydride and a diamine, and wherein the dianhydride is comprised of an aromatic dianhydride that has no rotational freedom within the dianhydride,
    (ii) heating the hollow polymer fiber to a carbonization temperature in an atmosphere that is non-oxidizing to form a hollow fiber carbon molecular sieve, wherein during at least a portion of the heating a tensile force is applied to the hollow polymer fiber along a length of the hollow polymer fiber to form the hollow fiber carbon molecular sieve membrane.

2. The method of claim 1, wherein the tensile force is applied throughout the heating of the fiber.

3. The method of claim 1, wherein the atmosphere is nitrogen, inert gas, mixture of any of the preceding gases, or mixture of the preceding gases having oxygen in an amount of less than 300 ppm.

4. The method of claim 1, wherein the tensile force is applied until a set elongation of the hollow polymer fiber is reached during the heating.

5. The method of claim 1, wherein prior to heating to the carbonization temperature, the hollow polymer fiber is heated to a pre-treatment temperature below the carbonization temperature.

6. The method of claim 5, wherein, at least during a portion of the heating to the pretreatment temperature, a tensile force is applied to the hollow polymer fiber.

7. The method of claim 1, wherein the polyimide has a storage modulus minimum at a temperature greater than 250° C. that is less than the storage modulus at a temperature of 250° C., but no more than ten times less measured using dynamic mechanical thermal analysis from 250° C. to a temperature where the polyimide carbonizes.

8. The method of claim 7, wherein the storage modulus minimum is at most 7.5 times less than the storage modulus at 250° C.

9. The method of claim 7, wherein the storage modulus minimum is at most 5 times less than storage modulus at 250° C.

10. The method of claim 1, wherein the dianhydride is comprised of the dianhydride that has no rotational freedom within the dianhydride and a diahydride that has rotational freedom within the dianhydride.

11. A method of making a hollow fiber carbon molecular sieve membrane comprising,
    (i) providing a hollow polymer fiber comprised of a polyimide,
    (ii) heating the hollow fiber polymer to a carbonization temperature in an atmosphere that is non-oxidizing to form a hollow fiber carbon molecular sieve, wherein during at least a portion of the heating a tensile force is applied to the hollow fiber along a length of the hollow polymer fiber to form the hollow fiber carbon molecular sieve membrane, wherein the polyimide is represented by:

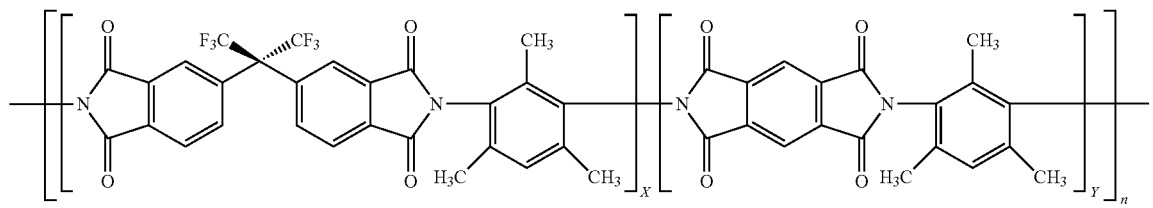

where X is 0.1 to 0.9 and Y is 0.1 to 0.9 and X+Y=1 and n is an integer that may be any that realizes a molecular weight of 30 to 200 kDa.

12. The method of claim 11, wherein X is 0.1 to 0.35 and Y is 0.65 to 0.9.

13. A process for separating a gas molecule from a gas feed comprised of the gas molecule and at least one other gas molecule comprising
   (i) providing the hollow fiber carbon molecular sieve produced by any one of the the method of claim 1; and
   (ii) flowing the gas feed through said hollow fiber carbon molecular sieve to produce a first stream having an increased concentration of the gas molecule and a second stream having an increased concentration of the other gas molecule.

14. The process of claim 13, wherein the gas molecule and other gas molecule is: hydrogen and ethylene; ethylene and ethane; propylene and propane; oxygen and nitrogen; hydrogen and methane; carbon dioxide and nitrogen; or carbon dioxide and methane.

15. The method of claim 14, wherein the gas molecule and other gas molecule is propylene and propane.

16. A gas separating module comprising a sealable enclosure comprised of: a plurality of hollow fiber carbon molecular sieves, comprising at least one hollow fiber carbon molecular sieve produced by the method of claim 1, contained within the sealable enclosure; an inlet for introducing a gas feed comprised of at least two differing gas molecules; a first outlet for permitting egress of a permeate gas stream; and a second outlet for egress of a retentate gas stream.

* * * * *